United States Patent [19]

Adamec

[11] 4,270,433
[45] Jun. 2, 1981

[54] FINGER RING WITH PLECTRUM

[76] Inventor: Robert Adamec, Georgenstrasse 49, 8450 Amberg, Fed. Rep. of Germany

[21] Appl. No.: 86,016

[22] Filed: Oct. 17, 1979

[30] Foreign Application Priority Data

Mar. 24, 1979 [DE] Fed. Rep. of Germany ....... 2911696
Aug. 14, 1979 [DE] Fed. Rep. of Germany ....... 2932882

[51] Int. Cl.³ .............................................. G10D 3/16
[52] U.S. Cl. ...................................................... 84/322
[58] Field of Search ........................................... 84/322

[56] References Cited

U.S. PATENT DOCUMENTS

| 557,293 | 3/1896 | Wahl | 84/322 |
| 1,573,912 | 2/1926 | Burdwise | 84/322 |
| 2,063,011 | 12/1936 | Bell | 84/322 |
| 3,595,118 | 7/1971 | Paxton | 84/322 |
| 3,789,720 | 2/1974 | McIntyre | 84/322 |

Primary Examiner—Lawrence R. Franklin
Attorney, Agent, or Firm—Jordan and Hamburg

[57] ABSTRACT

A plectrum ring comprises a ring element having a boss with a recess in the lower portion thereof dimensioned and configured to support therein the finger adjacent the finger wearing the ring element. A stud element projects upwardly from the boss for adjustably mounting a plectrum thereon, the axis of the stud element being substantially tangential to the finger wearing the ring element.

17 Claims, 14 Drawing Figures

U.S. Patent    Jun. 2, 1981    Sheet 1 of 2    4,270,433
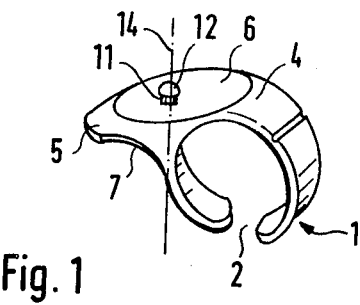
Fig. 1
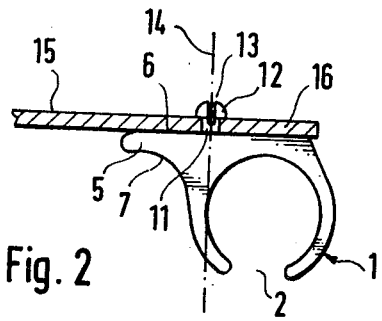
Fig. 2
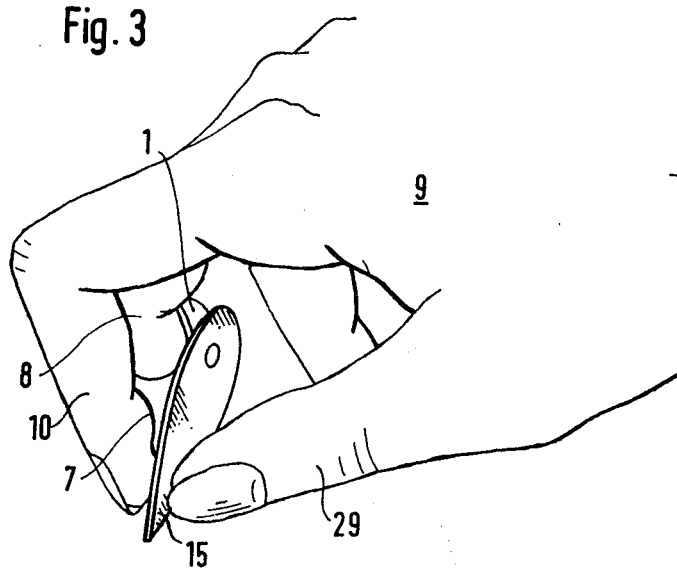
Fig. 3
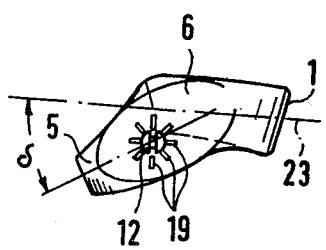
Fig. 4
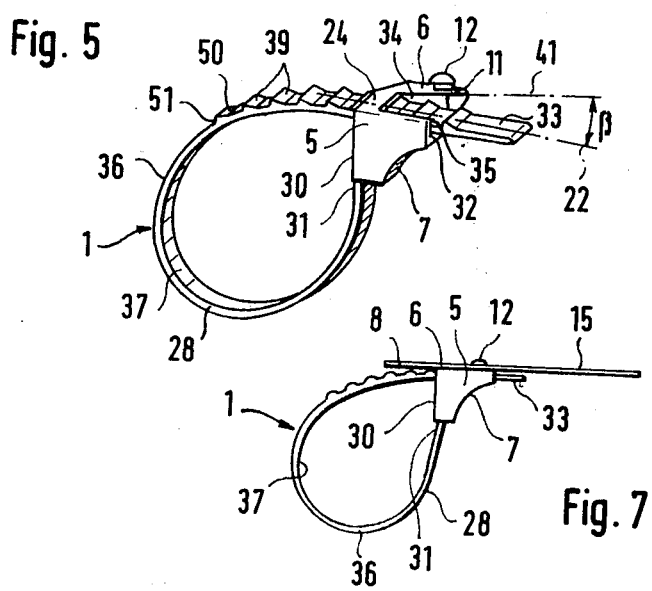
Fig. 5
Fig. 6
Fig. 7

U.S. Patent    Jun. 2, 1981    Sheet 2 of 2    4,270,433
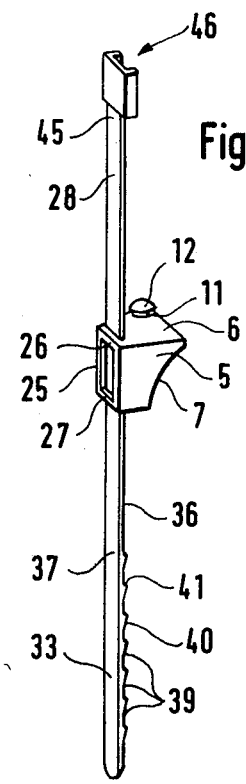
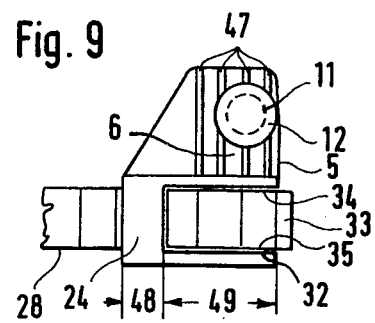
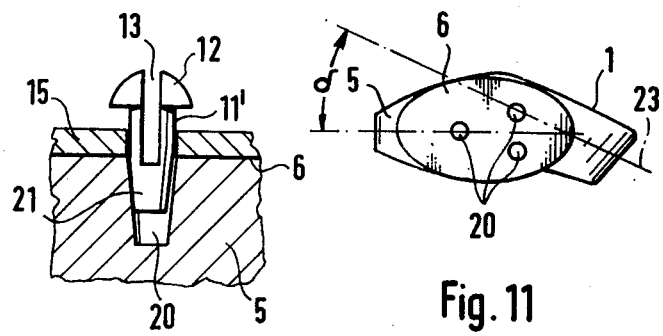
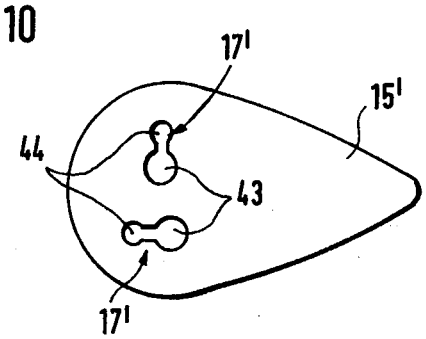
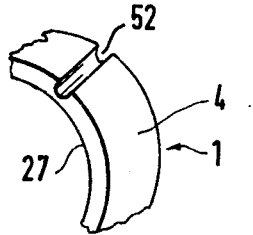
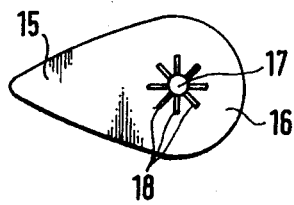

FINGER RING WITH PLECTRUM

BACKGROUND OF THE INVENTION

The invention relates generally to plectrum rings and more particularly to such rings in which the plectrum is adjustably supported upon a boss arranged on the ring.

Plectrums are used for plucking the strings of a string instrument such as a guitar. When a plectrum is used without a fastening ring it is easily lost, particularly during playing, and considerable inconvenience results. Attempts have been made to prevent loss of the plectrum by providing a finger ring which is positioned upon the end joint of the index finger and to which ring the plectrum is fastened by means of a riveted joint, a tubular rivet, a screw or the like. Frequently the plectrum is also made pivotable on the boss of the ring so that it may be shifted, if desired, into an inoperative position without removing the ring from the finger. U.S. Pat. No. 2,776,592 is noted in this regard. It has also been known to connect the plectrum to the ring by an arm as shown in U.S. Pat. No. 557,293 in order to facilitate working the plectrum while fastened to the ring using the index finger and the thumb. Finally, U.S. Pat. No. 3,789,720 shows an arrangement where stops are provided between the ring and the plectrum to enable positioning of the plectrum at a particular angle relative to the ring. Even if these known arrangements solve the problem of plectrum loss there still remain difficulties which are unresolved. One problem relates to the positioning of the plectrum for optimum handling and to reduce the element of finger fatigue. Furthermore, it is important that the player be able to readily substitute one plectrum for another when circumstances so demand such as a hard one for a soft one.

SUMMARY OF THE INVENTION

According to the invention a plectrum ring is provided having a boss and a recess therein for the support of another finger. The ring carries a stud whose axis extends tangentially to the finger wearing the ring.

Whereas the known plectrum rings are generally worn upon the index finger, which also coacts with the thumb as a guide for the plectrum, the ring of this invention enables reception of two different fingers. The ring is positioned upon one finger and the other finger is securely supported while still being sufficiently free to manipulate the plectrum in cooperation with the thumb. The ring is generally worn on the middle finger, particularly upon the second joint thereof while the recess in the boss serves as a prop for the adjacent index finger. In such manner the index finger remains sufficiently free so that it may be used without difficulty in gripping and holding the plectrum in conjunction with the thumb.

The ring may be formed in such a manner that the boss is disposed at the inner side of the finger so that the index finger may engage the recess loosely and obtain support therefrom while protruding from the recess so as to still be capable of gripping the plectrum on the side opposed to the thumb. Thus the index finger is supported and prevented from becoming fatigued. It was found that this particular arrangement of the axis relative to the finger resulted in greater comfort and ease of operation.

The invention provides for an arrangement of a stud upon a flat surface of the boss. The boss may be formed integrally with the ring and may, for instance, be made from a plastic material by injection molding. The flat surface of the plectrum is than very well supported by the flat surface of the boss. It was found to be particularly advantageous to dispose the boss in laterally staggered relationship to the plane of the ring which is particularly advantageous in respect to the anatomical structure of the hand. It is also easier and less stressfull to grip the plectrum.

Additional advantages of handling the plectrum result according to the invention when the surface of the boss which supports the stud is inclined at an acute angle to the plane of the ring and, additionally, at an acute angle to the outer side of the ring. This two fold inclination of the support surface for the plectrum facilitates an easy and exhaustion-free handling of the plectrum. Furthermore, according to another characteristic of the invention, the axis of the stud may form an acute angle with the plane of the ring. This takes into account the fact that the joint of the finger wearing the ring is slightly at an angle to the inner hand plane when the fingers are held in a relaxed position. Due to the fact that the axis of the stud forms an acute angle with the plane of the ring, the affect of this angular finger disposition upon the direction of the plectrum is compensated for. The plectrum is then oriented in the direction of the bisector of the angle between the finger joints leading the plectrum and the thumb. This is an especially advantageous position of the plectrum because the guiding pressure exerted by the fingers upon one side of the plectrum and by the thumb upon the other side of the plectrum is in equilibrium.

In another advantageous embodiment of the invention the ring consists of a band carrying the boss, one end of the band being securable in a closure part arranged at its other end. Thereby the size of the ring can be varied, its upper limit being determined by the length of the band. Due to the fact practically any flexible material may be used as the material of the band and that the length of the band may be freely chosen, the size of the ring can be smoothly adjusted between arbitrarily large and small diameters. It can thus be adapted to the anatomical structure of a variety of players and to the peculiarities of every finger or finger joint. Thus the ring can be adapted to its user and to any desired degree of tightness upon the finger of its user. In contradistinction to a rigid ring when the ring is employed in the form of a flexible band it is capable of conforming to the actual shape of a finger even in departure from a precise circular shape. Thus the ring-shaped band engages the finger at all points of its inner surface and is securely seated due to the frictional effect over its whole surface caused by this conformity. Thus, the invention creates on the one hand the best possible conditions for the manipulation of a plectrum ring and, since only one type of ring need be manufactured, unlike rings having a rigid diameter, a considerable reduction manufacturing cost and a reduction of stock is made possible.

In a particularly advantageous embodiment of the invention the band is connected to the boss, the latter including the closure member. Such an embodiment is easily produced because the complete ring, i.e., the band, boss and closure may be formed simultaneously in one piece in a conventional plastics manufacturing procedure. The large volume of the boss makes it particularly appropriate to provide the space needed and the substance needed for an exceptionally stable closure member.

Furthermore, it is very advantageous when the boss is provided with a guideway having an indentation for guiding and arresting the tongue shaped end of the band. The band may thus be easily and comfortably moved in this guideway in order to regulate the diameter of the ring until the desired size is obtained. It may then be easily arrested in this position by engaging the indentation provided by the guideway and by fastening it there.

According to the invention the outer edges of the boss are appreciably rounded, thereby simplifying finger engagement. Finally, it is also within the scope of the invention to movably guide the boss upon the band. That makes it possible to establish the position of the boss upon the band relative to its ends. This makes it possible for the user of the ring to fasten the closure part with the band arrested therein at a location of his finger circumference most convenient for him. In contradistinction to that the boss may be positioned at the appropriate place of the circumference of his finger independent of the position of the closure.

In order to obtain a secure connection between the plectrum and the ring, a frictional bearing may be provided between the plectrum and the ring. The plane upper surface of the boss around the stud is provided advantageously with a friction increasing surface. Another alternative provides such a friction increasing surface for the plectrum around a borehole which accepts the stud at the side adjacent this surface. Optionally both methods may be used simultaneously.

In order to make the ring or the plectrum better conform to the anatomical structure of the hand of a broad range of intended users the plectrum may be given several boreholes for selected acceptance of the stud. Then the plectrum extends for some distance over the ring. This principle may be reversed by making the stud arrestable at the boss of the ring, the ring being provided with several notches for the stud. In one preferred form the shank of the stud as well as the boreholes which accept the stud may be formed to be slightly conical so that secure seats for the studs are created.

In yet another advantageous embodiment of the invention the ring is provided on its outer peripheral surface with a transverse groove whose width is slightly smaller than the diameter of a guitar string. By the aid of this groove the ring, which may be provided with a plectrum when not in use, can be positioned on the string of a guitar so that it will not be lost.

BRIEF DESCRIPTION OF THE DRAWINGS

Additional characteristics and advantages of the invention will become clear from the following description which explains several preferred embodiments with the assistance of the drawings in which:

FIG. 1 is a perspective view of a plectrum ring, with the plectrum removed, embodying the features of the invention;

FIG. 2 is a side elevational view of the ring of FIG. 1 with the plectrum added;

FIG. 3 is a perspective view of the hand of a person wearing the ring with the plectrum in position to be used;

FIG. 4 is a top plan view of the ring with the plectrum removed;

FIG. 5 is a perspective view of a ring according to another embodiment with the plectrum removed;

FIG. 6 is a side elevational view in the plane of the ring, showing the ring of FIG. 5;

FIG. 7 is a side elevational view, normal to the plane of the ring, showing the embodiment of FIGS. 5 and 6 with the plectron added;

FIG. 8 is a perspective view of a modified band-type ring depicted in an opened condition;

FIG. 9 is a top plan view of the boss of the ring shown in FIG. 8;

FIG. 10 is a fragmentary side elevational view, in cross-section, of a portion of one form of boss and stud;

FIG. 11 is a view similar to that of FIG. 4 but of a modified boss;

FIG. 12 is a top plan view of one form of plectrum;

FIG. 13 is a bottom plan view of a suitable plectrum; and

FIG. 14 is a fragmentary perspective view of a portion of a modified ring.

DESCRIPTION OF THE PREFERRED EMBODIMENTS

Referring to the drawings, particularly FIGS. 1 and 2, there is shown a plectrum ring 1 which has a peripheral opening 2. It is, of course, within the ambit of the invention to utilize a fully closed ring without basically changing the character of the invention. The ring 1 is provided on its outer periphery with a boss 5 which is offset relative to the plane of the ring. The boss presents a flattened upper surface 6 and on its underside adjacent to the ring 1 proper with a shallow rounded recess 7. When the ring 1 is positioned upon the middle finger 8 of the hand 9, the inner side of the index finger 10 reposes in the recess 7.

Upon the plane surface 6 of the boss 5 a stud 11 is a disposed having a enlarged head 12 and if deemed advisable a transverse slot 13. The axis 14 of the stud 11 extends tangentially to the finger 8 which bears the ring 1.

A plectrum 15, which can take different shapes, is provided in its widened rear portion 16 with a borehole 17, whose internal diameter corresponds to the outer diameter of the stud 11 so that the plectrum 15 may be easily snapped onto the stud 11 but be retained securely therein. As shown in FIG. 13 the underside of the plectrum 15 is desirably provided with radial ribs 18 radiating from the borehole 17. The ribs are intended to coact with corresponding ribs 19 formed on the surface 6 of the boss 5 of the ring 1. These ribs 18 and/or 19 increase the friction between ring 1 and plectrum 15 and thereby prevent accidental swivelling of the plectrum 15 around the stud 11. It will be understood, of course, that the ribs may be provided on only one of the plectrum and boss.

The boss 5 may be arranged in the plane of the ring 3, as shown in the embodiments of FIGS. 1 and 3. On the other hand FIGS. 4 and 11 show that the boss 5 is disposed at an acute angle δ to the plane 23 of the ring 1 so that the boss 5 and the stud 11 are laterally offset relative to this plane 23 of the ring 1. The offset is desirably in the direction of the root of the finger 8 carrying the ring 1.

FIG. 10 depicts boss 5 with a conically tapered borehole 20 into which there is inserted the correspondingly conically formed shank 21 of stud 11'. If the surface 6 of the boss 5 is provided with several boreholes 20 as shown in FIG. 11 then stud 11' may be inserted in any one of them and in such a manner that the plectrum 15 occupies the most advantageous position for the individual player.

Plectrum 15' in FIG. 12 represents a modification where two boreholes 17' serve to fasten it at differing positions to the stud 11 of the ring 1. In the embodiment of FIG. 12 each borehole 17' consits of a longitudinal aperture having a portion 43 of a larger diameter such as the outer diameter of the head 12 of the stud, and a portion 44 with a smaller diameter which merges to portion 43 and has a diameter about the size of the diameter of the stud 11. The plectrum 15 can thus be made to rest upon the stud 11 in such a manner that the head 12 of the stud 11 at first enters the wider part 43 of the borehole 17' and then is arrested within the borehole part 44 by a lateral movement of the plectrum 15.

The embodiment of the ring shown in FIGS. 5 to 9 consists of a flexible band 28, shown in its ring-shaped form in FIGS. 5 to 7 and shown opened in FIG. 8. The boss 5 is formed at the outer peripheral side of the ring 1 and extends laterally from the plane 23 to the ring 1. Boss 5 is given a flat surface 6 which is tilted in a plane 40 forming an acute angle α with the plane 23 of the ring 1.

The boss 5 is rounded off at all its outer planes in order to assure unhindered abutting to the fingers of the hand 9. In FIG. 3 the second joint of the middle finger is inserted through the ring aperture formed by the band 28, while the first joint of the index finger 10 rests in the recess 7 of boss 5. The plectrum 15 is positioned for use between the thumb 29 and the index finger 10.

In the embodiment of FIGS. 5, 6 and 7, which may be manufactured in one piece out of a plastic material, the band 28 is connected by one end 31 to the underside of boss 5 close to the inner plane 30 at the underside of the boss 5. From there the band bends ring-shaped towards the flat surface 6 of boss 5 by virtue of its flexibility. Adjacent to the slightly elevated surface 6 of boss 5 there is formed a rectangular longitudinal slot 32, whose depth is slightly greater than the thickness of the band 28. This slot 32 serves as a guideway for the tongue shaped end 33 of the band 28 which can be moved longitudinally within the slot 32 and is thus guided between the sidewalls 34 and 35 thereof. A bridge 24 overlies the outer periphery 36 of band 28 which lies flatly on its inner surface 37 upon the base 38 of the slot 32. This bridge 24 serves as an indentation for the securing of the tongue-shaped end of band 28. The bridge 24 is disposed immediately at the entry end of the slot 32, whose length 49 (see FIG. 9) is a multiple of the length 48 of the bridge 24. Once the definite size of the ring has been determined by introduction of the band end 33 in the slot 32, the end of the band 28 projecting beyond slot 32 is cut off, so that it does not impede the playing of the instrument. In that manner there is always enough band present outside the bridge so that, if needed, the size of the ring 1, formed by the band 28, may be enlarged.

The tongue-shaped end 33 of the band 23 is provided on its outer surface 36 with a number of notches or serrations 39. They may be rounded in order to allow release of the band end 33. In the embodiment of FIG. 5 the notches 39 are formed by an obliquely rising flank 50 which merges into flank 51 of opposite inclination which descends steeply towards the outside surface 36.

In order to adjust the size of the ring 1, the band 28 (as shown especially in FIGS. 5 and 7) is threaded through the slot 32, in which case the obliquely rising flanks 50 can slide unhindered under the elastically yielding bridge 24. In this manner the band 28 is fed through the slot 32 until the desired ring diameter has been obtained. Then the steeper flank 51 of the respective notch 39 engages the bridge 24, thereby closing the ring 1.

FIG. 6 shows that the plane 23 of the ring 1 forms an acute angle δ' with the axis 14 of the stud 11. The boss 5 widens at the surface 6 by an outward curvature 42.

In contradistinction to the embodiment of FIGS. 5 to 7, where the boss 5 forms an integral part of the band 28, the boss 5 of FIG. 8 is disposed in the center of band 28 and may be connected to the band 28. For that purpose the boss 5 is provided in the area of its inner surface 25 with slits, formed by integrally connected bridges 26, 27. The band 28 is introduced through these slits and is thereby connected to the boss 5. At the end 45 of the band 28 there is provided a U-shaped closure member 46 corresponding substantially to the closure member of FIGS. 5 to 7. The surface 6 of the boss 5, carrying the plectrum 15, is provided as shown in FIG. 9 with ribs 47 in order to create sufficient friction between the plectrum 15 and the surface 6 to thereby prevent accidental swivelling of the plectrum on the stud.

As stated earlier the ring element 27 of the ring may be provided with a transverse slot 52 in its outer peripheral wall 4, the width of such slot being dimensioned to releasably retain a guitar string therein. Such construction enables the plectrum ring to be mounted on a guitar string of the instrument to minimize risk of loss.

What is claimed is:

1. A plectrum ring comprising a ring element and a plectrum, said ring element being adapted to be worn around the middle finger of a user, a boss carried by said ring element, and stud means pivotally mounting said plectrum on said boss, said stud means comprising a stud element having an axis which passes outside of said ring element such that the axis about which said plectrum pivots does not intersect said middle finger when the plectrum is worn by the user, whereby said plectrum is readily grasped between the index finger and the thumb of the user during use and is readily pivotable about said stud element while the ring element is still on the middle finger to permit the plectrum to be pivoted to a position removed from between the ends of the index finger and thumb to thereby free the index finger and thumb to pluck the strings of an instrument or the like while the plectrum is still retained on the middle finger.

2. A plectrum ring comprising a ring element and a plectrum, said ring element being adapted to be worn around the middle finger of a user, a boss carried by said ring element, and stud means mounting said plectrum on said boss, said stud means comprising a stud element having an axis about which said plectrum is pivotable, said stud means being constructed and arranged such that said axis of said stud element extends outside of said ring element.

3. A plectrum ring according to claim 2 wherein said axis of said stud element is disposed substantially tangential to said ring element.

4. A plectrum ring according to claim 2 wherein said boss has a planar surface and said stud element is carried by said planar surface.

5. A plectrum ring according to claim 4 wherein said axis of said stud element is perpendicular to said planar surface of said boss, said ring element having a ring plane which is defined as a plane which is perpendicular to the axis of the ring element and which passes through said ring element, said axis of said stud element intersecting said ring plane at an acute angle.

6. A plectrum ring according to claim 5 wherein said planar surface of said boss intersects said ring plane at an acute angle.

7. A plectrum ring according to claim 2 wherein said boss and the surface thereof carrying said stud element are off-set laterally at an acute angle relative to a ring plane which is perpendicular to the axis of the ring element and which passes through said ring element such that said plectrum pivots in a plane which is disposed at an acute angle relative to said ring plane.

8. A plectrum ring according to claim 2 wherein said boss has a recess dimensioned and configured to support thereagainst the index finger during use.

9. A plectrum ring according to claim 2 wherein said ring element comprises an elongated flexible band, and including a closure means to releasably retain one end portion of said band to form said ring element.

10. A plectrum ring according to claim 9 wherein said boss is integrally formed with said band and said closure means is part of said boss.

11. A plectrum ring according to claim 9 wherein said closure means comprises a guide slot extending longitudinally of said boss dimensioned to guidingly receive said one end of said band therein, said boss being provided with a bridge element overlying the entry end of said guide slot which is cooperable with said band for releasably retaining said band and thereby establishing a ring element of selected diameter.

12. A plectrum ring according to claim 11 comprising multiple serrations formed on the peripheral surface of said band, said serrations being so dimensioned and configured as to be cooperable with said bridge element for retaining the band in a selected position.

13. A plectrum ring according to claim 2, comprising means for increasing the frictional resistance between the contiguous surfaces of said plectrum and boss.

14. A plectrum ring according to claim 13, wherein said friction increasing means comprise rib elements formed on at least one of said contiguous surfaces.

15. A plectrum ring according to claim 2, comprising at least one bore hole in said plectrum and at least one bore hole in said boss dimensioned and configured to receive said stud element and thereby secure said plectrum to said boss.

16. A plectrum ring according to claim 2, comprising a transverse slot formed in the outer peripheral surface of said ring element, the width of said slot being dimensioned to releasably retain the string of a guitar therein.

17. A plectrum ring according to claim 2, wherein said ring element comprises an elongated flexible band and said boss is positioned slidably on said band.

* * * * *